(12) United States Patent
Multhoff (10) Patent No.: US 7,700,737 B2
(45) Date of Patent: Apr. 20, 2010

(54) THERAPEUTIC AND DIAGNOSTIC ANTI-HSP70 ANTIBODIES

(75) Inventor: Gabriele Multhoff, München (DE)

(73) Assignee: multimmune GmbH, Munich (DE)

( * ) Notice: Subject to any disclaimer, the term of this patent is extended or adjusted under 35 U.S.C. 154(b) by 409 days.

(21) Appl. No.: 10/581,960

(22) PCT Filed: Dec. 6, 2004

(86) PCT No.: PCT/EP2004/013854

§ 371 (c)(1),
(2), (4) Date: May 14, 2007

(87) PCT Pub. No.: WO2005/054295

PCT Pub. Date: Jun. 16, 2005

(65) Prior Publication Data

US 2007/0231337 A1  Oct. 4, 2007

(30) Foreign Application Priority Data

Dec. 5, 2003   (EP) .................................. 03028144

(51) Int. Cl.
*C07K 16/30* (2006.01)
*C12P 21/08* (2006.01)
*C12N 5/18* (2006.01)

(52) U.S. Cl. .............. 530/387.1; 530/387.3; 530/388.1; 435/326

(58) Field of Classification Search ....................... None
See application file for complete search history.

(56) References Cited

FOREIGN PATENT DOCUMENTS

| WO | WO 9116928 A1 * | 11/1991 |
| WO | WO 0222656 A2 * | 3/2002 |
| WO | WO 03/086383 | 10/2003 |
| WO | WO 2005/054868 | 6/2005 |

OTHER PUBLICATIONS

Botzler C et al, "Definition of extracellular localized epitopes of Hsp70 involved in an NK immune response," Cell Stress and Chaperones, Edinburgh, GB, vol. 3, 1998 pp. 6-11.

Multhoff G et al, "CD3-large granular lymphocytes recognize a heat-inducible immunogenic determinant associated with the 72-kD heat shock protein on human sarcoma cells," Blood, W.B. Saunders Phladelphia, VA vol. 86, Aug. 15, 1995, pp. 1374-1382.

Wei Yu-Quan et al, "Induction of autologous tumor killing bt heat treatment of fresh human tumor cells: Involvement of gamma-delta T cells and heat shock protein 70" Cancer Research,vol. 56 1996, pp. 1104-1110.

* cited by examiner

*Primary Examiner*—Ruixiang Li
(74) *Attorney, Agent, or Firm*—Casimir Jones, S.C.

(57) ABSTRACT

Methods and compositions for the detection, prevention and treatment of infectious diseases, primary and metastatic neoplastic diseases, including, but not limited to human sarcomas and carcinomas are described. In particular, specific antibodies are provided, which are capable of binding an epitope of Hsp70 that is extracellularly localized on diseased tissue and cells, in particular on tumor cells and infected cells.

11 Claims, 1 Drawing Sheet

Fig. 1

THERAPEUTIC AND DIAGNOSTIC ANTI-HSP70 ANTIBODIES

This application claims the benefit of European Patent Application No. EP 03 028 144.8, filed Dec. 5, 2003.

FIELD OF THE INVENTION

The present invention relates to methods and compositions for the detection, prevention and treatment of infectious diseases, primary and metastatic neoplastic diseases, including, but not limited to leukemia, human sarcomas and carcinomas. In accordance with the present invention, the practice of the detection, prevention and treatment of infectious diseases and cancer is mediated and/or indicated by the presence and localization of certain tumor markers on the cell surface of diseased tissue or cells. In particular, the present invention relates to antibodies and antigen-binding molecules which are capable of binding to an epitope of heat shock protein Hsp70 that is localized extracellularly on tumor cells. Furthermore, the present invention relates to compositions comprising said antibodies and their use in methods of diagnosis and treating immune response related and other diseases including tumors. The present invention further concerns the use of an antibody capable of recognizing membrane-bound Hsp70 protein or a binding domain thereof for the detection and/or treatment of a tumor or an infectious disease.

BACKGROUND OF THE INVENTION

Heat shock proteins (Hsps) are highly conserved molecules mediating protection against lethal damage following various stress stimuli in prokaryotic and eukaryotic cells. Also under physiological conditions they support folding of non-native or misfolded proteins and prevent aggregation during proliferation and cellular differentiation (Hartl and Hayer-Hartl, Science 295 (2002), 1852-1858). The best characterized group of chaperones belong to the Hsp70 family. Like other stress proteins, Hsp70s are most efficient if they operate in concert with co-factors as cellular chaperone machineries. Together with J domain co-chaperones (i.e. Hsp40), they support protein folding and assist translocation across membranes (Pilon and Schekman, Cell 97 (1999), 679-682). Heat shock proteins (HSP) are also inducible by physiological processes including cell differentiation and development (Lindquist and Craig, Annu. Rev. Genet. 22 (1988), 631). Intracellular HSP functions not only as molecular chaperones, they are involved in antigen processing and presentation as well (DeNagel and Pierce, Immunol. Today 13 (1992), 86; Hartl et al., Nature 381 (1996), 571). HSP with a molecular weight of 70 and 90 kDa also have been shown to function as carrier proteins for immunogenic tumor-derived peptides that induce a T cell mediated immune response against cancer (Tamura et al., Science 278 (1997), 117; Schild et al., Current Opinion in Immunology 11 (1999), 109; Srivastava et al., Immunity 8 (1998), 657). Antigen presenting cells are key for the receptor mediated uptake of HSP-peptide complexes (Arnold-Schild et al., J. Immunol. 162 (1999), 3757). Several groups reported an unusual plasma membrane localization of HSP on tumor cells (Altmeyer et al., Int. J. Cancer 69 (1996), 340; Ferrarini et al., Int. J. Cancer 51 (1992), 613; Piselli et al., J. Biol. Regul. Homeost Agents 9 (1995), 55; Tamura et al., J. Immunol. 151 (1993), 5516). The inventors were the first who demonstrated that NK cells also have to be considered as relevant effector cells for the recognition of membrane-bound Hsp70 on tumor cells (Multhoff et al., Blood 86 (1995a), 1374; Multhoff et al., Int. J. Cancer 61 (1995b), 272; Multhoff et al., J. Immunol. 158 (1997), 4341; Botzler et al., Cancer Immunol. Immunother. 43 (1996a), 226; Botzler et al., Int. J. Cancer 65 (1996b), 633). With respect to these findings and due to the fact that normal cells lack expression of Hsp70, on the plasma membrane, one might speculate that Hsp70 acts as a tumor-selective recognition structure for NK cells. Antibody blocking studies revealed that Hsp70 is a relevant recognition structure for transiently plastic adherent NK cells (Multhoff et al., Blood 86 (1995a), 1374; Multhoff et al., Int. J. Cancer 61 (1995b), 272; Multhoff et al., J. Immunol. 158 (1997), 4341; Botzler et al., Cell Stress & Chaperones 3 (1998), 6).

It was recently demonstrated that proliferation and cytolytic activity of NK cells against Hsp70-expressing tumor cells could be stimulated with recombinant Hsp70 protein but not with Hsc70 or DnaK (Multhoff et al., Exp. Hematology 27 (1999), 1627). As target cells for the cytolytic activity of NK cells the tumor sublines CX+ and CX− with an identical MHC and adhesion molecule expression pattern that differ with respect to the capacity to express Hsp70 on the plasma membrane, were used (Multhoff et al., J. Immunol. 158 (1997), 4341).

As described above, the presence and localization of Hsp70 on the cell surface of diseased tissue or cells, in particular on tumor cells provides a valuable marker and target for therapeutic intervention. It is thus highly desirable to have antibodies or other binding molecules, which specifically recognize extracellular epitopes of Hsp70 on such tissue and cells.

Although several antibodies directed against Hsp70 are commercially available and have been described in the literature, these appear to be uncapable and/or unreliable in detecting membrane-bound Hsp70 on the surface of cells. The inventors tested a panel of these antibodies for the ability to detect plasma membrane bound Hsp70. Most of the tested antibodies were unsuitable for this task (SPA-820, Stressgen; H553220-clone7; BD Pharmingen; H5147 clone BRM-22; Sigma; 0A500 polyclonal, Dako; MS-482 clone W27, NeoMarkers), while others gave conflicting results.

The anti-Hsp70 antibodies from Affinity Bioreagents (MA3-006 and MA3-009) showed different specificities for different batches. Some batches were suitable for the detection of Hsp70 on the plasma membrane to some extent (Botzler et al., Cell Stress & Chaperones 3 (1998), 6) but recent batches showed no reactivity towards Hsp70 localized on the cell surface of tumor cells. Similarly, clone C92F3A-5 supplied by Stressgen Inc. as SPA-810 and by MBL, Japan, as SR-B810 has been described to react with cell surface localized Hsp70 on some occasions (Barreto et al., Cell. Immunol. 222 (2003), 97-104; Feng et al., Blood 100 (2002), 4108-4115) but the inventors were unable to repeat the reported results. In the report of Feng et al. cell surface Hsp70 was only detected in apoptotic cells, which may be due to antibodies entering the degrading apoptotic cells whose cell membrane was no longer intact and detecting intracellular Hsp70. The conflicting results of Baretto et al and other investigators might further be due to quality differences of the batches used for the respective experiments. Also there are no reports of binding cell surface Hsp70 so far for the MBL supplied antibody.

Loss of specificity or a change of specificity of a monoclonal antibody may also be due the hybridoma cell line producing said antibody not being derived from a single cell line. A mixture of two or more different hybridomas will produce a mixture of two or more monoclonal antibodies with different specificity. The ratio of the cells within the culture and thereby the ratio of the different monoclonal antibodies produced by them may vary during cultivation. Also, a particular hybridoma producing the antibody with the desired specificity might be lost from the mixture if the other hybridoma cells have an evolutionary advantage. A mixture of hybridomas in the culture can also result from mutations in certain cells leading to shifting specificities of the antibodies produced.

Thus, there is a need for a reliable source of anti-Hsp70 antibodies capable of detecting extracellular epitopes of Hsp70 and thereby enabling the specific detection and treatment of tumor cells or cells infected by a pathogen.

The solution to said technical problem is achieved by providing the embodiments characterized in the claims and described further below.

SUMMARY OF THE INVENTION

The present invention relates to the technical field of immunology and the treatment of diseases mediated and/or indicated by the presence and localization of certain tumor markers on the cell surface of diseased tissue or cells. In a first aspect, the present invention relates to an antibody or antigen-binding fragment thereof that binds to an epitope of Hsp70 that is localized extracellularly on tumor cells.

Particularly, the present invention concerns a monoclonal antibody cmHsp70.1 as produced by hybridoma cmHsp70.1, deposited with the DSMZ—Deutsche Sammlung von Mikroorganismen und Zellkulturen GmbH, Mascheroder Weg 1b, D-38124 Braunschweig, Germany on Nov. 14, 2003, and assigned Accession Number DSM ACC2629, and cmHsp70.2 as well as the hybridoma producing it cmHsp70.2, deposited with the DSMZ—Deutsche Sammlung von Mikroorganismen und Zellkulturen GmbH on Nov. 14, 2003, and assigned Accession Number DSM ACC2630.

In a preferred embodiment, the antibody is a human, humanized, xenogeneic, or a chimeric human-murine antibody. Therapeutic compositions including the antibody or active fragments thereof, or agonists and cognate molecules, or alternately, antagonists of the same, and methods of use of such compositions in the prevention, diagnosis or treatment of tumorigenic or infections diseases using these compositions are also included, wherein an effective amount of the composition is administered to a patient in need of such treatment. However, for diagnostic uses and research in general murine antibodies are preferred as well.

The antigen-binding fragment of the monoclonal antibody can be a single chain Fv fragment, an F(ab') fragment, an F(ab) fragment, and an F(ab')$_2$ fragment, or any other antigen-binding fragment. In a specific embodiment, infra, the monoclonal antibody or fragment thereof is a murine IgG or IgM isotype antibody.

Naturally, the invention extends to the hybridoma that produces monoclonal antibody cmHsp70.1 or cmHsp70.2, which hybridoma is deposited with the DSMZ as indicated hereinbefore.

The present invention also relates to polynucleotides encoding at least a variable region of an immunoglobulin chain of the antibody of the invention. Preferably, said variable region comprises at least one complementarity determining region (CDR) of the $V_H$ and/or $V_L$ of the variable region of the antibody cmHsp70.1 or cmHsp70.2.

Accordingly, the present invention also encompasses vectors comprising said polynucleotides and host cells transformed therewith as well as their use for the production of an antibody capable of binding specifically extracellular localized epitopes of Hsp70 on intact cells, in particular tumor cells, or a functional fragment or immunoglobulin chain(s) thereof.

It is also an object of the invention to provide bi- or multifunctional molecules that comprise a binding domain of an antibody, an immunoglobulin chain or a binding fragment of the present invention, which binds cell surface membrane-bound heat shock protein (HSP), and at least one further functional domain.

The antibody, immunoglobulin chain(s), binding fragments thereof and ligands other than Hsp70 binding to said antibody can be used in pharmaceutical and diagnostic compositions for modulating and detecting an immune response or for the detection and/or treatment of a tumor.

Additionally, methods are provided for determining a tumor comprising assaying cells in a sample from a patient with the antibody or the bi- or multifunctional molecule according to the invention, wherein the presence or increased amount of extracellular localized Hsp70 is indicative for the tumor, and for treating a tumor or modulating the immune response in a subject in need thereof, comprising administering to the subject a therapeutically effective amount of said antibody or bi- or multifunctional molecule.

The use of the foregoing compositions in the preparation of medicament is preferred. In preferred embodiments, the medicament is useful in the treatment of conditions related to a tumor or an infections disease.

BRIEF DESCRIPTION OF THE DRAWINGS

FIG. 1: Hsp70 antibody of the invention block cytolytic activity of activated NK cells (NKd3). FIG. 1 shows the result of a representative experiment with monoclonal antibody cmHsp70.1. Either unstimulated (NKd0) or stimulated (NKd3) NK cells were used as effector cells at E:T ratios ranging from 20:1 to 2:1. Unstimulated NK cells (NKd3) showed only weak lysis of CX+ and CX− tumor cells, in contrast Hsp70 activated NK cells (NKd3) showed significant lysis of CX+ tumor cells but only weak lysis of CX− tumor target cells. After pre-incubation of CX+ and CX− tumor target cells with Hsp70 specific antibody (5 μg/ml) for 1 h and then used as target cells in a 4 h Cr-51 release assay, lysis of CX+ tumor cells (left graph) could be completely blocked by Hsp70 Ab whereas lysis of CX− target cells (right graph) remained unaffected. The data represent the mean values of three independent experiments +/−SE.

DETAILED DESCRIPTION OF THE INVENTION

The present invention concerns methods and compositions for the diagnosis, prevention and treatment of primary and metastatic neoplastic diseases and infectious diseases and for eliciting an immune response in a human individual. In particular, the present invention relates to molecules that bind to an extracellular localized epitope of Hsp70 on tumor cells, especially intact tumor cells. More specifically, the present invention relates to antibodies and antigen-binding fragments thereof, which demonstrate the immunological binding characteristics of monoclonal antibody cmHsp70.1 as produced by hybridoma cmHsp70.1, deposited with the DSMZ—Deutsche Sammlung von Mikroorganismen und Zellkulturen GmbH, Mascheroder Weg 1b, D-38124 Braunschweig, Germany on Nov. 14, 2003, and assigned Accession Number DSM ACC2629, or of cmHsp70.2 produced by the hybridoma cmHsp70.2, deposited with the DSMZ—Deutsche Sammlung von Mikroorganismen und Zellkulturen GmbH on Nov. 14, 2003, and assigned Accession Number DSM ACC2630. Where present, the term "immunological binding characteristics," or other binding characteristics of an antibody with an antigen, in all of its grammatical forms, refers to the specificity, affinity, cross-reactivity, and other binding characteristics of an antibody.

As mentioned before, while several antibodies specific for Hsp70 exist, only two of them have been reported to recognize occasionally an epitope that is localized extracellularly. The failure to bind to plasma membrane bound Hsp70 by its extracellular epitope might be due to either instability or varying quality of the antibody or to its requirement. for very specific binding conditions that are not always given.

Antibodies for diagnostic and/or therapeutic purposes however need to work reliably under various conditions encountered in routine laboratories and should be produced by a stable source, i.e. hybridoma cell line.

The present invention provides two hybridoma lines and the antibodies produced by them. It was surprisingly found that both purified antibodies are capable of binding to Hsp70 localized on the plasma membrane via an extracellular epitope. Since only transformed and infected human cells, respectively, appear to express Hsp70 on their cell surface the antibodies according to the invention are able to distinguish between normal and tumor cells. Thus, the invention provides an antibody or antigen-binding fragment thereof that binds to an extracellularly localized epitope of Hsp70 on tumor cells, which gives rise to several embodiments described herein.

Since the expression of Hsp70 on the cell surface is a hallmark of several different types of cancer, see supra while being absent from the plasma membrane of normal cells (Multhoff et al., Int. J. Cancer 61 (1995b), 272) a preferred embodiment of the antibody of the present invention binds to tumor cell, wherein said tumor is a human tumor selected from the group consisting of colon, lung, stomach, prancreas, head and neck, ovary, and/or breast cancer, melanoma, glioblastoma, sarcoma blastocytoma and/or hematological malignancies which are usually strongly correlated with tumor type and may play a role in earliest stages of tumor initiation, those hematological malignancies comprise Acute Myeloid Leukemia (AML), Myelodysplastic Syndromes (MDS), Myeloproliferative Disorders (MPD), Acute Lymphoblastic Leukemia (ALL), lymphomas such as Burkitt's lymphoma, Hodgkin's disease, non-Hodgkin's and non-Burkitt's lymphomas, and Lymphoproliferative Disorders (LPD), i.e. B- and T-lineage disorders.

In a preferred embodiment of the present invention, the antibodies recognize an epitope that comprises or consists of the amino acid sequence NLLGRFEL (SEQ ID NO: 1) or TKDNNLLGRFELSG (SEQ ID NO: 2. The peptides of SEQ ID NO: 1 and 2 were shown to be presented on the extracellular side of the plasma membrane when Hsp70 is localized on the cell surface and inhibit the binding of antibodies according to the invention in a dose dependent manner. Most preferably, said antibodies are monoclonal antibodies. In particular, the antibody or the antigen-binding fragment thereof of the present invention preferably exhibit the immunological binding characteristics of monoclonal antibody cmHsp70.1 as produced by hybridoma cmHsp70.1, deposited with the DSMZ—Deutsche Sammlung von Mikroorganismen und Zellkulturen GmbH, Mascheroder Weg 1b, D-38124 Braunschweig, Germany on Nov. 14, 2003, and assigned Accession Number DSM ACC2629, or of cmHsp70.2 as produced by the hybridoma cmHsp70.2, deposited with the DSMZ—Deutsche Sammlung von Mikroorganismen und Zellkulturen GmbH on Nov. 14, 2003, and assigned Accession Number DSM ACC2630. The immunological binding characteristics of monoclonal antibody cmHsp70.1 are substantially the same as those of antibody RPN1197 described inter alia in international patent application WO02/22656; see particularly the examples, the disclosure of which is incorporated herein by reference. However, while international application WO02/22656 as well as other publications by the inventors, e.g., Botzler et al., Cell Stress & Chaperones 3 (1998), 6-11, describe the desired immunological characteristics of an antibody of the present invention, especially that the antibodies are capable of binding to viable Hsp70-expressing (CX+) tumor cells and preferably also substantially inhibit the lysis of CX+ cells, the present invention for the first time enables the unlimited provision of such antibodies and reliable sources, in particular corresponding hyprodoma cell lines. Hence, the provision of the hybridomas producing monoclonal antibodies cmHsp70.1 and cmHsp70.2, respectively, enables the person skilled in the art to design and produce functionally equivalent antibodies, for example by adapting the antigen-binding site of either of the mentioned antibodies.

Figure 1:
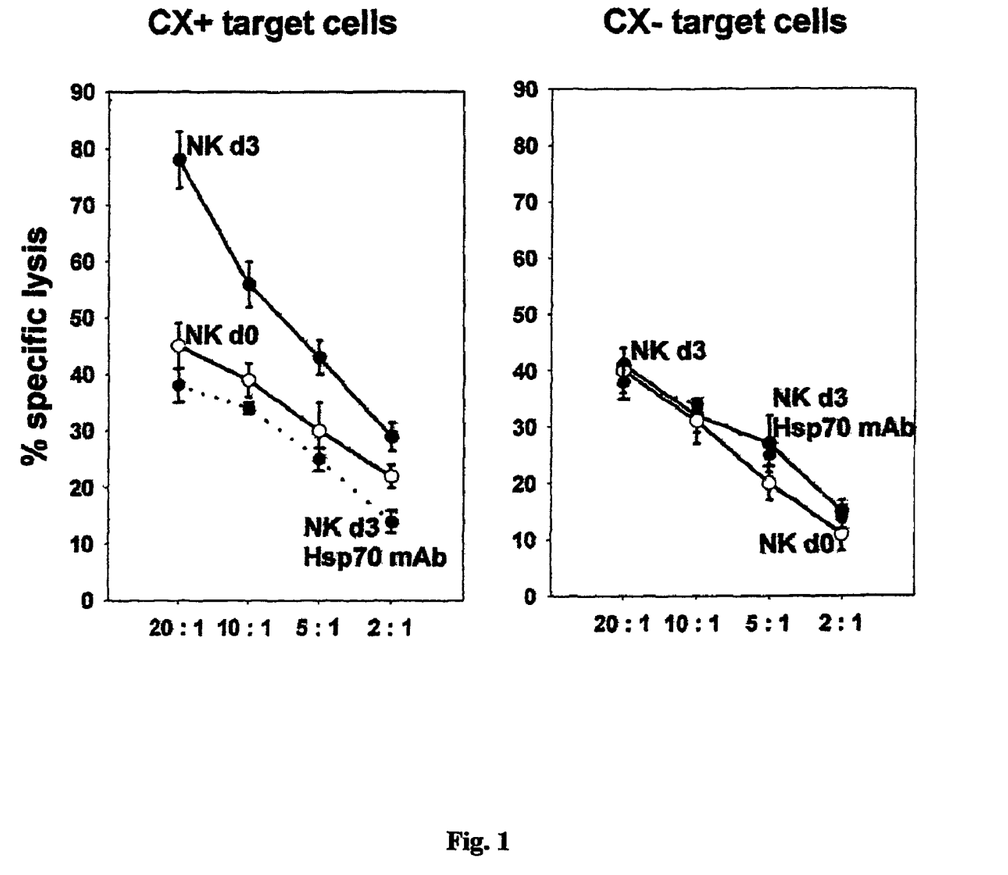

Each of the two antibodies specifically provided is unique with respect to its respective immunological and biological activities. Both may be distinguished from other anti-Hsp70 antibodies by their ability to bind to extracellular epitopes of Hsp70, in particular on intact and viable tumor cells. They are also capable of exhibiting an inhibitory effect on the cytolytic activity of NK cells against Hsp70 expressing tumor cells; see FIG. 1. Hence, Hsp70 binding molecules derived from cmHsp70.1 or from cmHsp70.2 are preferably used in but not limited to therapeutic and diagnostic applications.

Furthermore, in one embodiment the antibodies of the present invention are preferably characterized in that 0.1 to 10 μg/ml, preferably less than 5 μg/ml and most preferably about 0.1 to 1 μg/ml of the antibody of the invention is sufficient for the detection of CX tumor cells followed by protein A-bold labeling (10 μm Aurion) and viewed in a Zeiss EM 10CR electron microscope; see for experimental details, e.g., Botzler et al., Cell Stress & Chaperons 3 (1998), 6-11. Furthermore, the antibodies of the present invention are preferably characterized in that they are able to block the cytolytic activity of activated NK cells; see FIG. 1. In such experiments usually 1 to 20 μg/ml, preferably 5 to 10 μg/ml, and most preferably about or less than 5 μg/ml of the given antibody is sufficient to obtain the same results as described in FIG. 1.

Alternatively, the antibody of the present invention is a monoclonal antibody or antigen-binding fragment thereof, which competes for binding to an extracellular epitope of Hsp70 with an antibody provided by the present invention. Those antibodies may be murine as well; however, human, humanized, xenogeneic, or chimeric human-murine antibodies being preferred, in particular for therapeutic applications. An antigen-binding fragment of the antibody can be, for example, a single chain Fv fragment, an F(ab') fragment, an F(ab) fragment, and an F(ab')$_2$ fragment. Thus, for some applications only the variable regions of the antibodies are required, which can be obtained by treating the monoclonal antibody isolated from the hybridoma with suitable reagents so as to generate Fab', Fab, or F(ab")$_2$ portions. Such fragments are sufficient for use, for example, in immunodiagnostic procedures involving coupling the immunospecific portions of immunoglobulins to detecting reagents such as radioisotopes.

Naturally, the invention extends to the hybridoma producing antibodies according to the invention as well. Thus, the invention advantageously provides an indefinitely prolonged cell source of a monoclonal antibody of the invention: the hybridoma. Particularly preferred is a hybridoma selected from the group consisting of hybridoma cmHsp70.1, deposited with the DSMZ—Deutsche Sammlung von Mikroorganismen und Zellkulturen GmbH, Mascheroder Weg 1b, D-38124 Braunschweig, Germany on Nov. 14, 2003, and assigned Accession Number DSM ACC2629, or cmHsp70.2, deposited with the DSMZ—Deutsche Sammlung von Mikroorganismen und Zellkulturen GmbH on Nov. 14, 2003, and assigned Accession Number DSM ACC2670.

As an alternative to obtaining immunoglobulins directly from the culture of hybridomas, the immortalized hybridoma cells can be used as a source of rearranged heavy chain and light chain loci for subsequent expression and/or genetic manipulation. Rearranged antibody genes can be reverse transcribed from appropriate mRNAs to produce cDNA. If desired, the heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Once the genetic material is available, design of analogues as described above which retain both their ability to bind the desired target is straightforward. Methods for the cloning of antibody variable regions and generation of recombinant antibodies are known to the person skilled in the art and are described, for example, Gilliland et al., Tissue Antigens 47 (1996), 1-20; Doenecke et al., Leukemia 11 (1997), 1787-1792.

In accordance with the above, the present invention also relates to a polynucleotide encoding at least a variable region of an immunoglobulin chain of the antibody described above. Typically, said variable region encoded by the polynucleotide comprises at least one complementarity determining region (CDR) of the $V_H$ and/or $V_L$ of the variable region of the antibody produced by any one of the above described hybridomas. The person skilled in the art knows that each variable domain (the heavy chain $V_H$ and light chain $V_L$) of an antibody comprises three hypervariable regions, sometimes called complementarity determining regions or "CDRs" flanked by four relatively conserved framework regions or "FRs". The CDRs contained in the variable regions of the antibody of the invention can be determined, e.g., according to Kabat, Sequences of Proteins of Immunological Interest (U.S. Department of Health and Human Services, third edition, 1983, fourth edition, 1987, fifth edition 1990 and updates thereof). The person skilled in the art will readily appreciate that the variable domain of the antibody having the above-described variable domain can be used for the construction of other polypeptides or antibodies of desired specificity and biological function. Thus, the present invention also encompasses polypeptides and antibodies comprising at least one CDR of the above-described variable domain and which advantageously have substantially the same or similar binding properties as the antibody described herein above. The person skilled in the art will readily appreciate that using the variable domains or CDRs described herein antibodies can be constructed according to methods known in the art, e.g., as described in EP-A1 0 451 216 and EP-A1 0 549 581. Furthermore, the person skilled in the art knows that binding affinity may be enhanced by making amino acid substitutions within the CDRs or within the hypervariable loops (Chothia and Lesk, J. Mol. Biol. 196 (1987), 901-917) which partially overlap with the CDRs as defined by Kabat. Thus, the present invention also relates to antibodies wherein one or more of the mentioned CDRs comprise one or more, preferably not more than two amino acid substitutions.

The polynucleotide of the invention encoding the above described antibody may be, e.g., DNA, cDNA, RNA or synthetically produced DNA or RNA or a recombinantly produced chimeric nucleic acid molecule comprising any of those polynucleotides either alone or in combination. Preferably said polynucleotide is part of a vector. Such vectors may comprise further genes such as marker genes which allow for the selection of said vector in a suitable host cell and under suitable conditions.

Thus a vector comprising said polynucleotide, optionally in combination with a polynucleotide that encodes the variable region of the other immunoglobulin chain of said antibody is a preferred embodiment of the invention.

Preferably, the polynucleotide of the invention is operatively linked to expression control sequences allowing expression in prokaryotic or eukaryotic cells. Expression of said polynucleotide comprises transcription of the polynucleotide into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers, and/or naturally associated or heterologous promoter regions.

In this respect, the person skilled in the art will readily appreciate that the polynucleotides encoding at least the variable domain of the light and/or heavy chain may encode the variable domains of both immunoglobulin chains or only one. Likewise, said polynucleotides may be under the control of the same promoter or may be separately controlled for expression. Possible regulatory elements permitting expression in prokaryotic host cells comprise, e.g., the $P_L$, lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells.

Beside elements which are responsible for the initiation of transcription such regulatory elements may also comprise transcription termination signals, such as the SV40-poly-A site or the tk-poly-A site, downstream of the polynucleotide. Furthermore, depending on the expression system used leader sequences capable of directing the polypeptide to a cellular compartment or secreting it into the medium may be added to the coding sequence of the polynucleotide of the invention and are well known in the art. The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including a C- or N-terminal identification peptide imparting desired characteristics, e.g., stabilization or simplified purification of expressed recombinant product. In this context, suitable expression vectors are known in the art such as Okayama-Berg cDNA expression vector pcDV1 (Pharmacia), pCDM8, pRc/CMV, pcDNA1, pcDNA3 (Invitrogen), or pSPORT1 (GIBCO BRL).

Preferably, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and, as desired, the collection and purification of the immunoglobulin light chains, heavy chains, light/heavy chain dimers or intact antibodies, binding fragments or other immunoglobulin forms may follow; see, Beychok, Cells of Immunoglobulin Synthesis, Academic Press, N.Y., (1979).

Once the appropriate genetic material is obtained and, if desired, modified to encode an analogue, the coding sequences, including those that encode, at a minimum, the variable regions of the heavy and light chain, and inserted into an appropriate expression system, i.e. a vector which can be transfected, the antibody or fragment thereof may be expressed recombinantly in host cells. A variety of such host cells may be used; for efficient processing, however, mammalian cells are preferred. Typical mammalian cell lines useful for this purpose include CHO cells, 293 cells, or NSO cells.

A host cell comprising a polynucleotide or a vector according to the invention is thus a preferred embodiment. Vectors may be plasmids, cosmids, viruses and bacteriophages used conventionally in genetic engineering. Apart from a polynucleotide encoding a variable domain of an immunoglobulin chain of an antibody of the invention; they may optionally comprise a polynucleotide of the invention that encodes the variable domain of the other immunoglobulin chain of the antibody of the invention. Preferably, said vector is an expression vector and/or a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). Alternatively, the polynucleotides and vectors of the invention can be reconstituted into liposomes for delivery to target cells. The vectors containing the polynucleotides of the invention (e.g., the heavy and/or light variable domain(s) of the immunoglobulin chains encoding sequences and expression control sequences) can be transferred into the host cell by well known methods, which vary depending on the type of cellular host. For example, calcium chloride transfection is commonly utilized for prokaryotic cells, whereas calcium phosphate treatment or electroporation may be used for other cellular hosts; see Sambrook, supra The present invention furthermore relates to host cells transformed with a polynucleotide or vector of the invention. Said host cell may be a prokaryotic or eukaryotic cell. The polynucleotide or vector of the invention which is present in the host cell may either be integrated into the genome of the host cell or it may be maintained extrachromosomally. The host cell can be any prokaryotic or eukaryotic cell, such as a bacterial, insect, fungal, plant, animal or human cell. Preferred fungal cells are, for example, those of the genus *Saccharomyces*, in particular those of the species *S. cerevisiae*. The term "prokaryotic" is meant to include all bacteria which can be transformed or transfected with a DNA or RNA molecules for the expression of an antibody of the invention or the corresponding immunoglobulin chains. Prokaryotic hosts may include gram negative as well as gram positive bacteria such as, for example, *E. coli, S. typhimurium, Serratia marcescens* and *Bacillus subtilis*. The term "eukaryotic" is meant to include yeast, higher plant, insect and preferably mammalian cells, most preferably NSO and CHO cells. Depending upon the host employed in a recombinant production procedure, the antibodies or immunoglobulin chains encoded by the polynucleotide of the present invention may be glycosylated or may be non-glycosylated. Antibodies of the invention or the corresponding immunoglobulin chains may also include an initial methionine amino acid residue. A polynucleotide of the invention can be used to transform or transfect the host using any of the techniques commonly known to those of ordinary skill in the art. Furthermore, methods for preparing fused, operably linked genes and expressing them in, e.g., mammalian cells and bacteria are well-known in the art (Sambrook, Molecular Cloning: A Laboratory Manual, Cold Spring Harbor Laboratory, Cold Spring Harbor, N.Y., 1989). The genetic constructs and methods described therein can be utilized for expression of the antibody of the invention or the corresponding immunoglobulin chains in eukaryotic or prokaryotic hosts. In general, expression vectors containing promoter sequences which facilitate the efficient transcription of the inserted polynucleotide are used in connection with the host. The expression vector typically contains an origin of replication, a promoter, and a terminator, as well as specific genes which are capable of providing phenotypic selection of the transformed cells. Suitable source cells for the DNA sequences and host cells for immunoglobulin expression and secretion can be obtained from a number of sources, such as the American Type Culture Collection ("Catalogue of Cell Lines and Hybridomas," Fifth edition (1985) Rockville, Md., U.S.A., which is incorporated herein by reference). Furthermore, transgenic animals, preferably mammals, comprising cells of the invention may be used for the large scale production of the antibody of the invention.

The present invention also provides a method for preparing an antibody that binds to an extracellular localized epitope of Hsp70 on tumor cells, or a functional fragment or immunoglobulin chain(s) thereof, thereof, said method comprising
(a) culturing a cell described above; and
(b) isolating said antibody or functional fragment or immunoglobulin chain(s) thereof from the culture.

The expression systems are preferably designed to include signal peptides so that the resulting antibodies are secreted into the medium; however, intracellular production is also possible.

The transformed hosts can be grown in fermentors and cultured according to techniques known in the art to achieve optimal cell growth. Once expressed, the whole antibodies, their dimers, individual light and heavy chains, or other immunoglobulin forms of the present invention, can be purified according to standard procedures of the art, including ammonium sulfate precipitation, affinity columns, column chromatography, gel electrophoresis and the like; see, Scopes, "Protein Purification", Springer Verlag, N.Y. (1982). The antibody or its corresponding immunoglobulin chain(s) of the invention can then be isolated from the growth medium, cellular lysates, or cellular membrane fractions. The isolation and purification of the, e.g., microbially expressed antibodies or immunoglobulin chains of the invention may be by any conventional means such as, for example, preparative chromatographic separations and immunological separations such as those involving the use of monoclonal or polyclonal antibodies directed, e.g., against the constant region of the antibody of the invention. It will be apparent to those skilled in the art that the antibodies of the invention can be further coupled to other moieties for, e.g., drug targeting and imaging applications. Such coupling may be conducted chemically after expression of the antibody or antigen to site of attachment or the coupling product may be engineered into the antibody or antigen of the invention at the DNA level. The DNAs are then expressed in a suitable host system, and the expressed proteins are collected and renatured, if necessary.

Substantially pure immunoglobulins of at least about 90 to 95% homogeneity are preferred, and 98 to 99% or more homogeneity most preferred, for pharmaceutical uses. Once purified, partially or to homogeneity as desired, the antibodies may then be used therapeutically (including extracorporeally) or in developing and performing assay procedures.

The present invention also involves a method for producing cells capable of expressing an antibody of the invention or its corresponding immunoglobulin chain(s) comprising genetically engineering cells with the polynucleotide or with the vector of the invention. The cells obtainable by the method of the invention can be used, for example, to test the interaction of the antibody of the invention with its antigen.

Furthermore, the present invention relates to a method of obtaining antibodies from hybridomas comprising a novel purification protocol as outlined in example 2. While commont purification protocols may be used for obtaining antibodies of the invention, they may be less effective than the method described in example 2. Historically, Protein A has been the preferred method of immunoglobulin purification. However, there are certain types of antibodies, such as the single-chain antibodies IgE, IgY and IgM that cannot be purified using the Protein A. An alternative method of immunoglobulin purification, thiophilic adsorption chromatography, is ideal for these types of applications, as well as immunoglobulin purification in general. For general references relating to protein purification procedures including purification of immunoglobulins see for example the booklet from BD Biosciences Clontech, Pablo Alto, Calif., USA, www-.clontech.com. Based on previous methods using thiophilic agarose a novel purification protocol has been established in accordance with the present invention, which is particularly suitable for obtaining antibodies of the type IgG1, IgG2a and IgM from hybridomas, particular those hybridomas producing antibodies of the present invention being described herein. However, it is to be understood that the novel method for the purification of antibodies is generally applicable and thus is also subject of the present invention. For experimental details, see example 2. In this respect, it is also to be understood that methods for obtaining antibodies including the purification protocol as described in example 2, which may have minor modifications, e.g., in the composition of the respective buffers, wherein a deviation of +/−10% of the concentration of the different ingredients may be tolerable, are also encompassed in the scope of the present invention as well. Furthermore, the present invention relates to antibodies obtained by the novel method described herein as well as to binding fragments of such antibodies. Naturally, the present invention also extends to derivatives of such antibodies and binding fragments such as those described herein.

As mentioned before, the immunoglobulin or its encoding cDNAs may be further modified. Thus, in a further embodiment the method of the present invention comprises any one of the step(s) of producing a chimeric antibody, humanized antibody, single-chain antibody, Fab-fragment, bi-specific antibody, fusion antibody, labeled antibody or an analog of any one of those. Corresponding methods are known to the person skilled in the art and are described, e.g., in Harlow and Lane "Antibodies, A Laboratory Manual", CSH Press, Cold Spring Harbor, 1988. When derivatives of said antibodies are obtained by the phage display technique, surface plasmon resonance as employed in the BIAcore system can be used to increase the efficiency of phage antibodies which bind to the same epitope as that of any one of the antibodies described herein (Schier, Human Antibodies hybridomas 7 (1996), 97-105; Malmborg, J. Immunol. Methods 183 (1995), 7-13). The production of chimeric antibodies is described, for example, in WO89/09622. Methods for the production of humanized antibodies are described in, e.g., EP-A1 0 239 400 and WO90/07861. A further source of antibodies to be utilized in accordance with the present invention are so-called xenogeneic antibodies. The general principle for the production of xenogeneic antibodies such as human antibodies in mice is described in, e.g., WO 91/10741, WO 94/02602, WO 96/34096 and WO 96/33735. As discussed above, the antibody of the invention may exist in a variety of forms besides complete antibodies; including, for example, Fv, Fab and F(ab)$_2$, as well as in single chains; see, e.g., WO88/09344.

The antibodies of the present invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). Modifications of the antibody of the invention include chemical and/or enzymatic derivatizations at one or more constituent amino acids, including side chain modifications, backbone modifications, and N- and C-terminal modifications including acetylation, hydroxylation, methylation, amidation, and the attachment of carbohydrate or lipid moieties, cofactors, and the like. Likewise, the present invention encompasses the production of chimeric proteins which comprise the described antibody or some fragment thereof at the amino terminus fused to heterologous molecule such as an immunostimulatory ligand at the carboxyl terminus; see, e.g., WO00/30680 for corresponding technical details.

Additionally, the present invention encompasses small polypeptides including those containing a Hsp70 binding fragment as described above, for example containing the CDR3 region of the variable region of any one of the mentioned monoclonal antibodies. Such peptides may easily be synthesized or produced by recombinant means to produce a Hsp70 binding agent useful according to the invention. Such methods are well known to those of ordinary skill in the art. Peptides can be synthesized for example, using automated peptide synthesizers which are commercially available. The peptides can be produced by recombinant techniques by incorporating the DNA expressing the peptide into an expression vector and transforming cells with the expression vector to produce the peptide. The sequence of the CDR regions, for use in synthesizing peptide Hsp70 binding agents, may be determined by methods known in the art. The heavy chain variable region is a peptide which generally ranges from 100 to 150 amino acids in length. The light chain variable region is a peptide which generally ranges from 80 to 130 amino acids in length. The CDR sequences within the heavy and light chain variable regions which include only approximately 3-25 amino acids may easily be sequenced by one of ordinary skill in the art. The peptides may even be synthesized by commercial sources.

To determine whether a peptide binds to Hsp70 any known binding assay may be employed. For example, the peptide may be immobilized on a surface and then contacted with labeled Hsp70. The amount of Hsp70 which interacts with the peptide or the amount which does not bind to the peptide may then be quantitated to determine whether the peptide binds to Hsp70. A surface having the aforementioned anti-Hsp70 monoclonal antibodies immobilized thereto may serve as a positive control.

Screening of Hsp70 binding agents also can be carried out utilizing a competition assay. If the Hsp70 binding agent being tested competes with an anti-Hsp70 monoclonal antibody of the present invention, as shown by a decrease in binding of the monoclonal antibody, then it is likely that the agent and the anti-Hsp70 monoclonal antibody bind to the same, or a closely related, epitope. Still another way to determine whether an agent has the specificity of the anti-Hsp70 monoclonal antibodies described above is to pre-incubate the monoclonal antibody with Hsp70 with which it is normally reactive (i.e., binds), and then add the agent being tested to determine if the agent being tested is inhibited in its ability to bind Hsp70. If the agent being tested is inhibited then, in all likelihood, it has the same or a functionally equivalent epitope and specificity as the anti-Hsp70 monoclonal antibodies.

Using routine procedures known to those of ordinary skill in the art, one can determine whether a Hsp70 binding agent is useful according to the invention by determining whether the agent is one which modulates T cell proliferation or cytotoxicity in an in vitro assay such as measuring release of TNF from T cells or by $^{51}$Cr release assay; see, e.g., Herin et al., Int. J. Cancer 39 (1987), 390-396. Other assays are described in the Examples and elsewhere herein; see also WO02/22656.

The polypeptides (e.g. antibodies) and other Hsp70 binding agents described above can also be used immunotherapeutically for disorders in humans. The term "immunotherapeutically" or "immunotherapy" as used herein in conjunction with the Hsp70 binding agents denotes both prophylactic as well as therapeutic administration. Thus, the peptides can be administered to high-risk subjects in order to lessen the likelihood and/or severity of a disease such as a tumor, or infectious disease, or administered to subjects already evidencing such diseases.

Hsp70 binding agents which increase or decrease NK cell activity can be selected using the assays described, for example, in WO02/22656 and according to standard killer cell cytotoxicity and proliferation assays, such as mixed lymphocyte reactions, chromium release assays, TNF release assays, and thymidine incorporation assays. It is believed that a monovalent Hsp70 binding agent, for example derivatives of single chain antibodies which have only one binding domain of the original antibody, will inhibit the stimulatory signal of Hsp70 by reducing Hsp70 polypeptides expressed by target cells.

Hence, the present invention relates to any antibody and similar binding molecules, which preferably have substantially the same immunological binding characteristics as monoclonal antibodies cmHsp70.1 or cmHsp70.2, i.e. which recognize the same epitope and with substantially the same affinity, or at least $\frac{1}{10}$ of the affinity as the antibodies of the invention exemplified herein. Such antibodies and binding molecules can be tested for their binding specificity and affinity by for example by using competitive assays with an antibody produced by a hybridoma of the invention. The antibodies of the present invention will typically find use individually in treating substantially any disease susceptible to monoclonal antibody based therapy. In particular, the immunoglobulins can be used as immunosuppressive agents. For an antibody of the invention, typical disease states suitable for treatment include inflammatory symptoms. The antibodies can be used therapeutically in, e.g., patients suffering an diseases related to immune response; see supra. Such therapy can be accomplished by, for example, the administration of antibodies of the invention.

Such administration can utilize unlabeled as well as labeled antibodies or antigens. Labeling agents can be coupled either directly or indirectly to the antibodies or antigens of the invention. One example of indirect coupling is by use of a spacer moiety. Furthermore, the antibodies of the present invention can comprise a further domain, said domain being linked by covalent or non-covalent bonds. The linkage can be based on genetic fusion according to the methods known in the art and described above or can be performed by, e.g., chemical cross-linking as described in, e.g., WO 94/04686. The additional domain present in the fusion protein comprising the antibody of the invention may preferably be linked by a flexible linker, advantageously a polypeptide linker, wherein said polypeptide linker comprises plural, hydrophilic, peptide-bonded amino acids of a length sufficient to span the distance between the C-terminal end of said further domain and the N-terminal end of the antibody of the invention or vice versa. The above described fusion protein may further comprise a cleavable linker or cleavage site for proteinases. These spacer moieties, in turn, can be either insoluble or soluble (Diener et al., Science 231 (1986), 148) and can be selected to enable drug release from the antigen at the target site. Examples of therapeutic agents which can be coupled to the antibodies, antigens and epitopes of the invention for immunotherapy are drugs, radioisotopes, lectins, and toxins. The drugs with which can be conjugated to the antibodies, antigens and epitopes of the invention include compounds which are classically referred to as drugs, such as mitomycin C, daunorubicin, and vinblastine. In using radioisotopically conjugated antibodies, antigens or epitopes of the invention for, e.g., immunotherapy, certain isotopes may be more preferable than others depending on such factors as leukocyte distribution as well as stability and emission. Depending on the autoimmune response, some emitters may be preferable to others. In general, $\alpha$ and $\beta$ particle emitting radioisotopes are preferred in immunotherapy. Preferred are short range, high energy a emitters such as $^{212}$Bi. Examples of radioisotopes which can be bound to the antibodies, antigens or epitopes of the invention for therapeutic purposes are $^{125}$I, $^{131}$I, $^{90}$Y, $^{67}$Cu, $^{212}$Bi, $^{212}$At, $^{211}$Pb, $^{47}$Sc, $^{109}$Pd and $^{188}$Re. Other therapeutic agents which can be coupled to the antibody, antigen or epitope of the invention, as well as ex vivo and in vivo therapeutic protocols, are known, or can be easily ascertained, by those of ordinary skill in the art. Wherever appropriate the person skilled in the art may use a polynucleotide of the invention encoding any one of the above described antibodies, antigens or the corresponding vectors instead of the proteinaeous material itself.

As described above, the polynucleotide of the invention can be used alone or as part of a vector to express the (poly) peptide of the invention in cells. In principle this also enables gene therapy of diseases related to inappropriate expression of Hsp70 on the plasma membrane. For example, it is envisaged to introduce a polynucleotide or a vector of the invention into a cell of the immune system, preferably a cytotoxic killer cell in order to enable the cell to express a receptor comprising the binding domain of an antibody of the present invention, which renders the cell capable of recognizing specifically tumor cells or other diseased cells, which express Hsp70 on their cell surface. The polynucleotides or vectors of the invention are introduced into the cells which in turn produce the antibody or corresponding receptor molecules. Gene therapy, which is based on introducing therapeutic genes into cells by ex-vivo or in-vivo techniques is one of the most important applications of gene transfer. Suitable vectors and methods for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813; Isner, Lancet 348 (1996), 370-374;

Muhlhauser, Circ. Res. 77 (1995), 1077-1086; Wang, Nature Medicine 2 (1996), 714-716; WO94/29469; WO 97/00957 or Schaper, Current Opinion in Biotechnology 7 (1996), 635-640, and references cited therein. The polynucleotides and vectors of the invention may be designed for direct introduction or for introduction via liposomes, or viral vectors (e.g. adenoviral, retroviral) into the cell. Preferably, said cell is a germ line cell, embryonic cell, or egg cell or derived therefrom, most preferably said cell is a stem cell.

Plasma membrane bound Hsp70 interacts with other cell surface molecules, and it is reasonable to assume that agents modulating these interactions will have beneficial, additive and preferably synergistic effects on the treatment of diseases and conditions, wherein either of these proteins are involved in. Furthermore, such agents are expected to be useful in diagnosis, where the presence or absence of either of said proteins is associated with said disease or condition. Accordingly, the present invention also provides novel bi- or multifunctional molecules that comprise the binding domain of an antibody according to the invention, an immunoglobulin chain thereof or a binding fragment thereof which bind cell surface membrane-bound heat shock protein (HSP70), and at least one further functional domain; see also supra. In a preferred embodiment said bi- or multifunctional molecule is bispecific molecule, particularly preferred a bispecific antibody.

The term "bispecific molecule" includes molecules which have at least the two mentioned binding domains directly or indirectly linked by physical or chemical means. However, the bispecific molecule of the present invention may comprise further functional domains such as additional binding domains and/or moieties such as a cytotoxic agent or a label and the like; see also supra.

Means and methods for the preparation of multivalent, multispecific molecules having at least one specificity for a desired antigen are known to the person skilled in the art. For example, WO99/59633 describes multimeric molecules with at least one specificity for the HLA class II invariant chain (Ii) and their use for the clearance of therapeutic or diagnostic agents, autoantibodies, anti-graft antibodies, and other undesirable compounds. As used herein, unless otherwise indicated or clear from the context, antibody or binding domains, regions and fragments are accorded standard definitions as are well known in the art; see, e.g., Abbas et al., Cellular and Molecular Immunology (1991), W. B. Saunders Company, Philadelphia, Pa.

Certain bispecific molecules of the present invention are used for binding to antigen or to block interaction of a protein and its ligand; their use to promote interactions between immune cells and target cells however is preferred. Finally, antigen-binding molecules of the invention are used to localize immune cells, tumor cells, infected cells, anti-tumor agents, target moieties, reporter molecules or detectable signal producing agents to an antigen of interest.

Bispecific molecules of the invention can cross-link antigens on target cells with antigens on immune system effector cells. This can be useful, for example, for promoting immune responses directed against cells which have a particular antigens of interest on the cell surface. According to the invention, immune system effector cells include antigen specific cells such as T cells which activate cellular immune responses and nonspecific cells such as macrophages, neutrophils and natural killer (NK) cells which mediate cellular immune responses. Hence, bispecific molecules of the invention can have a further binding site for any cell surface antigen of an immune system effector cell. Such cell surface antigens include, for example, cytokine and lymphokine receptors, Fc receptors, CD3, CD16, CD28, CD32, CD64 and CD94. In general, antigen binding sites are provided by scFvs which are derived from antibodies to the aforementioned antigens and which are well known in the art. Antigen-binding sites of the invention which are specific for cytokine and lymphokine receptors can also be sequences of amino acids which correspond to all or part of the natural ligand for the receptor. For example, where the cell-surface antigen is an IL-2 receptor, an antigen-binding protein of the invention can have an antigen-binding site which comprises a sequence of amino acids corresponding to IL-2. Other cytokines and lymphokines include, for example, interleukins such as interleukin-4 (IL-4), interleukin-5 (IL-5), interleukin-15 (IL-15) and colony-stimulating factors (CSFs) such as granulocyte-macrophage CSF (GM-CSF), and granulocyte CSF (G-CSF).

In addition, any one of the described bispecific molecules may contain a binding domain binding FcgammaRI on activated effector cells. The clinical potential of this approach for the treatment of tumors such as B cell malignancies looks most attractive. Triggering of antitumor immunity by expression of anti-FcgammaR scFv on cancer cell surface has been described by Gruel et al., Gene Ther. 8 (2001), 1721-1728.

In addition or alternatively, the bispecific molecule of the invention may comprise a binding domain binding CD3. This embodiment is particularly useful for the treatment of carcinoma; see, e.g., Riesenberg et al., J. Histochem. Cytochem. 49 (2001), 911-917, which report on the lysis of prostate carcinoma cells by trifunctional bispecific antibodies (alpha EpCAM×alpha CD3).

These and other combinations of functional domains in the bispecific molecule of the present invention and uses thereof are encompassed by the present invention.

In a preferred embodiment, the bispecific molecule of the present invention is a bispecific antibody. The bispecific antibodies may comprise Fc constant regions, for example for association of the polypeptide chains comprising the binding domains. In addition to providing for association of the polypeptide chains, Fc constant domains contribute other immunoglobulin functions. The functions include activation of complement mediated cytotoxicity, activation of antibody dependent cell-mediated cytotoxicity and Fc receptor binding. When antigen-binding proteins of the invention are administered for treatment or diagnostic purposes, the Fc constant domains can also contribute to serum halflife. The Fc constant domains can be from any mammalian or avian species. When antigen binding proteins of the invention are used for treatment of humans, constant domains of human origin are preferred, although the variable domains can be non-human. In cases where human variable domains are preferred, chimeric scFvs can be used. Further means and methods for the production of bispecific antibodies are described in the art; see, e.g., WO97/14719 which describes a process for producing bispecific or bivalent double head antibody fragments, which are composed of a binding complex containing two polypeptide chains, and WO01/80883. Furthermore, the bispecific molecules of the invention can be optimized in their avidity for antigen(s) while maintaining their ability to function as a natural antibody, including the ability to activate complement mediated cytotoxicity and antibody dependent cellular toxicity; see, e.g., WO01/90192.

Furthermore, the present invention relates to a composition comprising, the antibody, the bi- or multifunctional molecule, the polynucleotide or the above described vector or cell of the invention. The composition of the present invention may further comprise a pharmaceutically acceptable carrier.

Additionally moieties may be added that improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical or intradermal administration. Aerosol formulations such as nasal spray formulations include purified aqueous or other solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 μg (or of nucleic acid for expression or for inhibition of expression in this range); however, doses below or above this exemplary range are envisioned, especially considering the aforementioned factors. Generally, the regimen as a regular administration of the pharmaceutical composition should be in the range of 1 μg to 10 mg units per day. If the regimen is a continuous infusion, it should also be in the range of 1 μg to 10 mg units per kilogram of body weight per minute, respectively. Progress can be monitored by periodic assessment. Dosages will vary but a preferred dosage for intravenous administration of DNA is from approximately $10^6$ to $10^{12}$ copies of the DNA molecule. The compositions of the invention may be administered locally or systemically. Administration will generally be parenterally, e.g., intravenously; DNA may also be administered directly to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Furthermore, the pharmaceutical composition of the invention may comprise further agents such as interleukins or interferons depending on the intended use of the pharmaceutical composition. Furthermore, the pharmaceutical composition may also be formulated as a vaccine, for example, if the pharmaceutical composition of the invention comprises a bispecific molecule described above for passive immunization.

Therapeutic or diagnostic compositions of the invention are administered to an individual in a therapeutically effective dose sufficient to treat or diagnose disorders as mentioned above. The effective amount may vary according to a variety of factors such as the individual's condition, weight, sex and age. Other factors include the mode of administration. The pharmaceutical compositions may be provided to the individual by a variety of routes such as by intracoronary, intraperitoneal, subcutaneous, intravenous, transdermal, intrasynovial, intramuscular or oral routes. In addition, co-administration or sequential administration of other agents may be desirable. A therapeutically effective dose refers to that amount of active molecule of the invention sufficient to ameliorate the symptoms or condition. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

The pharmaceutical composition of the present invention further comprises an immune stimulatory agent in a preferred embodiment. Immune stimulatory agents are used to enhance an immune reaction or to induce an immune reaction against epitopes which do not trigger an humoral or cytotoxic defense reaction under normal conditions. Such agents are well known in the art and can be chosen from a wide variety of molecules such as co-stimulatory molecules, e.g. cytokines and/or adjuvants.

An "adjuvant" refers to a substance that enhances an immune response, including, for example, but not limited to, an antigen's immune-stimulating properties or the pharmacological effect(s) of a compound or drug. An adjuvant may non-specifically enhance an immune response, e.g., the immune response to an antigen. "Freund's Complete Adjuvant," for example, is an emulsion of oil and water containing an immunogen, an emulsifying agent and mycobacteria. Another example, "Freund's incomplete adjuvant," is the same, but without mycobacteria. An adjuvant may comprise oils, emulsifiers, killed bacteria, aluminum hydroxides or calcium phosphate (e.g. in gel form), or combinations thereof. An adjuvant may be administered into a subject (e.g., via injection intramuscularly or subcutaneously) in an amount sufficient to produce antibodies. Comparison of the effect of different immunological adjuvants on the antibody and T-cell response to immunization with MUC1-KLH and GD3-KLH conjugate cancer vaccines in the mouse has been described in Kim et al., Vaccine 18 (1999), 597-603. In this publication also ELISA assays for IgM and IgG antibody responses as well as proliferation and cytokine release (IFN-gamma and IL-4) for T-cell responses are described, which can also be performed in accordance with the present invention.

The present invention also refers to a diagnostic composition comprising an antibody, a bi- or multifunctional molecule, a polynucleotide, a vector or a cell according to the invention; and optionally reagents conventionally used in immuno or nucleic acid based diagnostic methods. For use in diagnosis, a variety of techniques are available for labeling biomolecules, are well known to the person skilled in the art and are considered to be within the scope of the present invention. Such techniques are, e.g., described in Tijssen, "Practice and theory of enzyme immuno assays", Burden, R H and von Knippenburg (Eds), Volume 15 (1985), "Basic methods in molecular biology"; Davis L G, Dibmer M D; Battey Elsevier (1990), Mayer et al., (Eds) "Immunochemical methods in cell and molecular biology", Academic Press, London (1987), or in the series "Methods in Enzymology", Academic Press, Inc. There are many different labels and methods of labeling known to those of ordinary skill in the art. Commonly used labels comprise, inter alia, fluorochromes (like fluorescein, rhodamine, Texas Red, etc.), enzymes (like horse radish peroxidase, β-galactosidase, alkaline phosphatase), radioactive isotopes (like $^{32}P$ or $^{125}I$), biotin, digoxygenin, colloidal metals, chemi- or bioluminescent compounds (like dioxetanes, luminol or acridiniums). Labeling procedures, like covalent coupling of enzymes or biotinyl groups, iodinations, phosphorylations, biotinylations, random priming, nick-translations, tailing (using terminal transferases) are well known in the art. Detection methods comprise, but are not limited to, autoradiography, fluorescence microscopy, direct and indirect enzymatic reactions, etc.

In addition, the above described compounds etc. may be attached to a solid phase. Solid phases are known to those in the art and may comprise polystyrene beads, latex beads, magnetic beads, colloid metal particles, glass and/or silicon chips and surfaces, nitrocellulose strips, membranes, sheets, animal red blood cells, or red blood cell ghosts, duracytes and the walls of wells of a reaction tray, plastic tubes or other test tubes. Suitable methods of immobilizing bispecific molecules of the invention on solid phases include but are not limited to ionic, hydrophobic, covalent interactions and the like. The solid phase can retain one or more additional receptor(s) which has/have the ability to attract and immobilize the region as defined above. This receptor can comprise a charged substance that is oppositely charged with respect to the reagent itself or to a charged substance conjugated to the capture reagent or the receptor can be any specific binding partner which is immobilized upon (attached to) the solid phase and which is able to immobilize the reagent as defined above.

Commonly used detection assays can comprise radioisotopic or non-radioisotopic methods. These comprise, inter alia, RIA (Radioisotopic Assay) and IRMA (Immune Radioimmunometric Assay), EIA (Enzym Immuno Assay), ELISA (Enzyme Linked Immuno Assay), FIA (Fluorescent Immuno Assay), and CLIA (Chemiluminescent Immune Assay). Other detection methods that are used in the art are those that do not utilize tracer molecules. One prototype of these methods is the agglutination assay, based on the property of a given molecule to bridge at least two particles.

Nucleic acid based diagnostic format are also well known to the person skilled in the art and include, but are not limited to, hybridization of Southern or Northern blots, PCR, sequencing, RFLP and SSCP analyses.

The present invention also relates to a kit comprising an antibody or a bispecific molecule of the invention. Such kits are useful for a variety of purposes including but not limited to forensic analyses, diagnostic applications, and epidemiological studies in accordance with the above described diseases and disorders. Such a kit would typically comprise a compartmentalized carrier suitable to hold in close confinement at least one container. The carrier would further comprise reagents for detection such as labeled antigen or enzyme substrates or the like.

Naturally the present invention also encompasses a method of diagnosing a tumor comprising assaying cells in a sample from a patient with the antibody, or the bi- or multifunctional molecule according to the invention, wherein the presence or increased amount of extracellular localized Hsp70 is indicative for the tumor.

This method preferably comprises an immunological step. Commonly used diagnostic methods employing antibodies and/or bi- or multifunctional molecules are for example immunohistochemistry on frozen or paraffin embedded tissue sections, Western blots, immunoprecipitation etc. Optionally, easy to detect signal producing agents can be used in conjunction with said antibodies or bi- or multifunctional molecules.

Detectable signal-producing agents are useful in vivo and in vitro for diagnostic purposes. The signal producing agent produces a measurable signal which is detectable by external means, usually the measurement of electromagnetic radiation. For the most part, the signal producing agent is an enzyme or chromophore, or emits light by fluorescence, phosphorescence or chemiluminescence. Chromophores include dyes which absorb light in the ultraviolet or visible wavelength range, and can be substrates or degradation products of enzyme catalyzed reactions.

As described before, the compositions of the present invention are useful in diagnosis, prophylaxis, vaccination or therapy. Accordingly, the present invention relates to the use of the antibody, the bi- or multifunctional molecule, the nucleic acid molecule or the cell of the present invention for the preparation of a pharmaceutical composition for the treatment of a tumor or modulating an immune response.

For these embodiments, the antibodies or the bi- or multifunctional molecules of the invention can be chemically or biosynthetically linked to anti-tumor agents or detectable signal-producing agents; see also supra. Antitumor agents linked to a bispecific molecule, for example a bispecific antibody, include any agents which destroy or damage a tumor to which the antibody has bound or in the environment of the cell to which the antibody has bound. For example, an anti-tumor agent is a toxic agent such as a chemotherapeutic agent or a radioisotope. Suitable chemotherapeutic agents are known to those skilled in the art and include anthracyclines (e.g. daunomycin and doxorubicin), methotrexate, vindesine, neocarzinostatin, cis-platinum, chlorambucil, cytosine arabinoside, 5-fluorouridine, melphalan, ricin and calicheamicin. The chemotherapeutic agents are conjugated to the antibody using conventional methods; see, e.g., Hermentin and Seiler, Behring Inst. Mitt. 82 (1988), 197-215. A method of treating a tumor or modulating the immune response in a subject in need thereof, usually comprises administering to the subject a therapeutically effective amount of the antibody or the bi- or multifunctional molecule. As mentioned above, a therapeutically effective dose refers to that amount of active molecule of the invention sufficient to ameliorate the symptoms or condition. Therapeutic efficacy and toxicity of such compounds can be determined by standard pharmaceutical procedures in cell cultures or experimental animals; see also supra.

For the purpose of this invention said pharmaceutical composition is preferably designed to be administered intravenously, intramuscularly, subcutaneously, intraperitoneally, or as an aerosol.

Preferably, the tumor to be treated or diagnosed is selected from the group consisting of carcinomas of lung, colorectum, pancreas, larynx, stomach, head, neck, breast, ovaries, uterine, cervix, liver, peripheral and central nervous system, sarcomas, chronic myeloic leukemia (CML), acute myeloic leukemia (AML), acute lymphatic leukemia (ALL), non Hodgkin Lymphoma (NHL), myeloproliferative syndrome (MPS), myelodysplastic syndrome (MDS), plasmocytoma, melanoma and metastatic cells in general.

Also encompassed by the uses and methods of the present invention are disorders related to an immune response which include, but are not limited to a viral infections, bacterial infections, rheumatoid arthritis, lupus erythematodes, asthma bronchiale etc.

The terms "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e. arresting its development; or (c) relieving the disease, i.e. causing regression of the disease.

Furthermore, the term "subject" as employed herein relates to animals in need of amelioration, treatment and/or prevention of a neoplastic or infectious disease. Most preferably said subject is a human.

Since the exclusive expression of Hsp70 on the surface of disease related cells, the invention provides the means for the targeted delivery to these cells while avoiding the normal cells. This is of particular advantage if toxic moieties are linked to a therapeutic molecule as described above. Such a method of targeting a therapeutic and/or diagnostic agent to a cell which expresses an extracellular localized epitope of Hsp70 on the cell surface comprises administering to the subject a therapeutically effective amount of a bi- or multifunctional molecule of the invention. The use of a bi- or multifunctional molecule for targeting a therapeutic and/or diagnostic agent to a cell which expresses an extracellular localized epitope of Hsp70 on the cell surface is, of course, a preferred embodiment of this invention. Said targeted cell can either be preferably a tumor cell or a cell related to an immune disorder or an infectious disease.

From the foregoing, it is evident that the present invention encompasses any use of a ligand binding molecule comprising at least one CDR of the above described antibody, in particular for diagnosing and/or treatment of a disorder related to the expression or malfunction of Hsp70 on the cell surface of target cells, in particular tumor cells or infected cells. Preferably, said ligand binding molecule is an antibody of the present invention or an immunoglobulin chain thereof. In addition, the present invention relates to anti-idiotypic antibodies of any one of the mentioned monoclonal antibodies described hereinbefore. These are antibodies or other binding molecules which bind to the unique antigenic peptide sequence located on an antibody's variable region near the antigen binding site. One concept for immune therapy of cancer involves induction of antigen mimic antibodies to trigger the immune system into a response against the tumor cells. Anti-idiotypic antibodies (Ab2) directed against the antigen-combining site of other antibodies (Ab1) may functionally and even structurally mimic antigen and induce anti-anti-idiotypic immune response. An example of functional mimicry of an anti-idiotypic antibody to a murine monoclonal immunoglobulin (Ab1), which defines ovarian cancer antigen CA125, is described in Ma et al., Jpn. J. Cancer Res. 93 (2002), 78-84. A murine monoclonal anti-idiotypic antibody as a surrogate antigen for human Her-2/neu is described in Baral et al., Int. J. Cancer 92 (2001), 88 95. Further examples comprise active immunotherapy with anti-idiotypic antibody for patients with nasopharyngeal carcinoma (NPC), described by Li et al., Cancer Biother. Radiopharm. 17 (2002), 673-679 and anti-idiotypic antibodies carrying the "internal image" of peptide YIGSR inhibit spontaneous metastasis of Lewis lung carcinoma in mice described by Koliakos et al. in In Vivo 16 (2002), 511-518. Preferably, the anti-idiotypic antibody is humanized; see also supra.

The biological activity of the antibodies identified here suggests that they have sufficient affinity to make them potential candidates for drug localization to cells expressing the appropriate surface structures. This targeting and binding to cells could be useful for the delivery of therapeutically or diagnostically active agents (including targeting drugs, DNA sequences, RNA sequences, lipids, proteins (e.g., human growth factors)) and gene therapy/gene delivery. Molecules/particles with an antibody of the invention would bind specifically to cells/tissues expressing Hsp70 on the cell surface, and therefore could have diagnostic and therapeutic use. Thus, the antibody or the antigen of the present invention can be labeled (e.g., fluorescent, radioactive, enzyme, nuclear magnetic) and used to detect specific targets in vivo or in vitro including "immunochemistry" like assays in vitro. In vivo they could be used in a manner similar to nuclear medicine imaging techniques to detect tissues, cells, or other material expressing Hsp70, in particular on the cell surface of target cells. Another method involves delivering a therapeutically active agent to a patient. The method includes administering at least one antibody or the antigen-binding fragment and the therapeutically active agent to a patient. Preferably, the therapeutically active agent is selected from drugs, DNA sequences, RNA sequences, proteins, lipids, and combinations thereof. More preferably, the therapeutically active agent is an antibacterial agent, anti-inflammatory agent, or antineoplastic agent.

The therapeutically or diagnostically active agent can be coupled to the antibody of the invention or an antigen-binding fragment thereof by various means. This includes, for example, single-chain fusion proteins comprising the variable regions of the antibody of the invention coupled by covalent methods, such as peptide linkages, to the therapeutically or diagnostically active agent. Further examples include molecules which comprise at least an antigen-binding fragment coupled to additional molecules covalently or non-covalently include those in the following non-limiting illustrative list. Traunecker, Int. J. Cancer Surp. SuDP 7 (1992), 51-52, describe the bispecific reagent janusin in which the Fv region directed to CD3 is coupled to soluble CD4 or to other ligands such as OVCA and IL-7. Similarly, the variable regions of the antibody of the invention can be constructed into Fv molecules and coupled to alternative ligands such as those illustrated in the cited article. Higgins, J. Infect Disease 166 (1992), 198-202, described a hetero-conjugate antibody composed of OKT3 cross-linked to an antibody directed to a specific sequence in the V3 region of GP120. Such hetero-conjugate antibodies can also be constructed using at least the variable regions contained in the antibody of the invention methods. Additional examples of specific antibodies include those described by Fanger, Cancer Treat. Res. 68 (1993), 181-194 and by Fanger, Crit. Rev. Immunol. 12 (1992), 101-124. Conjugates that are immunotoxins including conventional antibodies have been widely described in the art. The toxins may be coupled to the antibodies by conventional coupling techniques or immunotoxins containing protein toxin portions can be produced as fusion proteins. The antibodies of the present invention can be used in a corresponding way to obtain such immunotoxins. Illustrative of such immunotoxins are those described by Byers, Seminars Cell. Biol. 2 (1991), 59-70 and by Fanger, Immunol. Today 12 (1991), 51-54.

The invention further contemplates linking molecules of the invention to target or reporter moieties. Target moieties are first members of binding pairs. Anti-tumor agents, for example, are conjugated to second members of such pairs and are thereby directed to the site where the antigen-binding protein is bound. A common example of such a binding pair is adivin and biotin. Biotin can be conjugated to an molecule of the invention, and thereby provides a target for an anti-tumor agent or other moiety which is conjugated to avidin or streptavidin. Alternatively, biotin or another such moiety is linked to a molecule of the invention and used as a reporter, for example in a diagnostic system where a detectable signal-producing agent is conjugated to avidin or streptavidin. Suitable radioisotopes for use as anti-tumor agents are also known to those skilled in the art. For example, $^{131}$I or $^{211}$At is used. These isotopes are attached to the antibody using conventional techniques; see, e.g., Pedley et al., Br. J. Cancer 68 (1993), 69-73. Alternatively, the anti-tumor agent which is attached to the antibody is an enzyme which activates a pro-drug. In this way, a prodrug is administered which remains in its inactive form until it reaches the tumor site where it is converted to its cytotoxic form once the antibody complex is administered. In practice, the antibody-enzyme conjugate is administered to the patient and allowed to localize in the region of the tissue to be treated. The prodrug is then administered to the patient so that conversion to the cytotoxic drug occurs in the region of the tissue to be treated. Alternatively, the anti-tumor agent conjugated to the antibody is a cytokine such as interleukin-2 (IL-2), interleukin-4 (IL-4), interleukin-15 (IL-15) or tumor necrosis factor alpha (TNF-α). The antibody targets the cytokine to the tumor so that the cytokine mediates damage to or destruction of the tumor without affecting other tissues. The cytokine is fused to the antibody at the DNA level using conventional recombinant DNA techniques.

By a further embodiment as mentioned before, the ligand binding molecules and antibodies of the invention may also be used in a method for the diagnosis of Hsp70-related diseases in an individual by obtaining a body fluid sample from the tested individual which may be a blood sample, a lymph sample or any other body fluid sample and contacting the body fluid sample with an antibody of the invention under conditions enabling the formation of antibody-antigen complexes. Similarly, biopsy or other specimen may be taken common in tumor diagnostic. The level of such complexes is then determined by methods known in the art, a level significantly higher than that formed in a control sample indicating the disease in the tested individual. In the same manner, the specific antigen bound by the antibodies of the invention may also be used. Thus, the present invention relates to an in vitro immunoassay comprising the antibody or the antigen of the invention.

These and other embodiments are disclosed and encompassed by the description and examples of the present invention. Further literature concerning any one of the materials, methods, uses and compounds to be employed in accordance with the present invention may be retrieved from public libraries and databases, using for example electronic devices. For example the public database "Medline" may be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person skilled in the art and can also be obtained using internet search engines. An overview of patent information in biotechnology and a survey of relevant sources of patent information useful for retrospective searching and for current awareness is given in Berks, TIBTECH 12 (1994), 352-364.

The contents of all cited references (including literature references, issued patents, published patent applications as cited throughout this application and manufacturer's specifications, instructions, etc) are hereby expressly incorporated by reference; however, there is no admission that any document cited is indeed prior art as to the present invention.

The above disclosure generally describes the present invention. A more complete understanding can be obtained by reference to the following specific examples which are provided herein for purposes of illustration only and are not intended to limit the scope of the invention.

EXAMPLES

The examples which follow further illustrate the invention, but should not be construed to limit the scope of the invention in any way. Detailed descriptions of conventional methods, such as those employed herein can be found in the cited literature; see also "The Merck Manual of Diagnosis and Therapy" Seventeenth Ed. ed by Beers and Berkow (Merck & Co., Inc. 2003).

The practice of the present invention will employ, unless otherwise indicated, conventional techniques of cell biology, cell culture, molecular biology, transgenic biology, microbiology, recombinant DNA, and immunology, which are within the skill of the art. Particularly useful means and methods for the recombinant production of bispecific molecules are described in WO94/13804, WO01/80883 and WO01/90192. All references mentioned herein are incorporated in their entirety.

Methods in molecular genetics and genetic engineering are described generally in the current editions of Molecular Cloning: A Laboratory Manual, (Sambrook et al., (1989) Molecular Cloning: A Laboratory Manual, 2nd ed., Cold Spring Harbor Laboratory Press); DNA Cloning, Volumes I and II (Glover ed., 1985); Oligonucleotide Synthesis (Gait ed., 1984); Nucleic Acid Hybridization (Hames and Higgins eds. 1984); Transcription And Translation (Hames and Higgins eds. 1984); Culture Of Animal Cells (Freshney and Alan, Liss, Inc., 1987); Gene Transfer Vectors for Mammalian Cells (Miller and Calos, eds.); Current Protocols in Molecular Biology and Short Protocols in Molecular Biology, 3rd Edition (Ausubel et al., eds.); and Recombinant DNA Methodology (Wu, ed., Academic Press). Gene Transfer Vectors For Mammalian Cells (Miller and Calos, eds., 1987, Cold Spring Harbor Laboratory); Methods In Enzymology, Vols. 154 and 155 (Wu et al., eds.); Immobilized Cells And Enzymes (IRL Press, 1986); Perbal, A Practical Guide To Molecular Cloning (1984); the treatise, Methods In Enzymology (Academic Press, Inc., N.Y.); Immunochemical Methods In Cell And Molecular Biology (Mayer and Walker, eds., Academic Press, London, 1987); Handbook Of Experimental Immunology, Volumes I-IV (Weir and Blackwell, eds., 1986). Reagents, cloning vectors, and kits for genetic manipulation referred to in this disclosure are available from commercial vendors such as BioRad, Stratagene, Invitrogen, and Clontech. General techniques in cell culture and media collection are outlined in Large Scale Mammalian Cell Culture (Hu et al., Curr. Opin. Biotechnol. 8 (1997), 148); Serum-free Media (Kitano, Biotechnology 17 (1991), 73); Large Scale Mammalian Cell Culture (Curr. Opin. Biotechnol. 2 (1991), 375); and Suspension Culture of Mammalian Cells (Birch et al., Bioprocess Technol. 19 (1990), 251); Extracting information from cDNA arrays, Herzel et al., CHAOS 11, (2001), 98-107.

Example 1

Providing Hybridomas Expressing cmHsp70.1 and cmHsp70.2

Mice were immunized with peptide TKDNNLLGR-FELSG (SEQ ID NO: 2) and boosted according to an improved protocol by the inventors. After establishing several cell-lines producing antibodies that could be determined to recognize Hsp70, two hybridomas could be identified that produce antibodies capable of binding an epitope of Hsp70 that is localized extracellularly on tumor cells. In particular, cmHsp70.1 as produced by hybridoma cmHsp70.1, deposited with the DSMZ—Deutsche Sammlung von Mikroorganismen und Zellkulturen GmbH, Mascheroder Weg 1b, D-38124 Braunschweig, Germany on Nov. 14, 2003, and assigned Accession Number DSM ACC2629, and cmHsp70.2 as produced by hybridoma cmHsp70.2, deposited with the DSMZ—Deutsche Sammlung von Mikroorganismen und Zellkulturen GmbH on Nov. 14, 2003, and assigned Accession Number DSM ACC2630 are provided. The anti-Hsp70 antibody produced by hybridoma cmHsp70.1 was determined to be an IgG-type immunoglobulin while the anti-Hsp70 antibody produced by hybridoma cmHsp70.2 is an IgM-type immunoglobulin.

Example 2

Purification of Antibodies cmHsp70.1 and cmHsp70.2 by Thiophilic Chromatography Since previous protocols for purification of immunoglobulins turned out to be cumbersome for the purification of anti-Hsp70 antibodies, a novel purification protocol has been established, comprising hydrophobic interaction chromatography (HIC) and the following materials and methods.

| Material | |
|---|---|
| Column material: | T-Gel ™ Adsorbent (Pierce, Product number: 20500) |
| Volume: | 10 ml |
| Binding capacity: | 20 mg immunoglobulins/ml gel |
| Wet bead diameter: | 45-165 μm (6% beaded agarose) |

Äkta Prime FPLC system (Amersham Biosciences)

Supernatants were derived from approx. 1000 ml Hybridoma supernatant from clone cmHsp70.1 or cmHsp70.2, cultured in RPMI1640/10% FCS or DEMEM/20% FCS, respectively. Supernatants from 48 h incubations at a starting cell density of $0.2 \times 10^6$ cells/ml were harvested and centrifuged at 300×g (5 min, 4° C.) following a 1000×g centrifugation (5 min, 4° C.). The supernatants were stored at 4° C.

Chemicals were obtained by Sigma ($Na_3PO_4$;$NaN_3$) or Roth (($NH_4$)$_2SO_4$;Tris), all buffer were made with millipore water.

| Buffers | |
|---|---|
| Binding buffer: | 0.5M ammonium sulfate, 50 mM sodium phosphate and 0.05% sodium azide, pH 8.0 |
| | 16.5 g $(NH_4)_2SO_4$ |
| | 1.78 g $Na_3PO_4$ |
| | 125 mg $NaN_3$ |
| | pH 8.0, ad 250 ml |
| Elution buffer: | 50 mM sodium phosphate and 0.05% sodium azide, pH 8.0 |
| | 1.78 g $Na_3PO_4$ |
| | 125 mg $NaN_3$ |
| | pH 8.0, ad 250 ml |
| Storage buffer: | 0.5M Tris and 0.02% sodium azide, pH 7.4 |
| | 15.1 g Tris |
| | 50 mg $NaN_3$ |
| | pH 7.4, ad 250 ml |

Sample Preparation

While mixing, 66 mg of ammonium sulfate were added per ml of clarified hybridoma supernatant; see supra. The final concentration was 0.5 M ammonium sulfate in the sample. The hybridoma supernatant was gently mixed to avoid denaturation of immunoglobulins by local high salt concentration or air. When the ammonium sulfate is fully dissolved, the sample was adjusted to pH 8.0 and centrifuged at 1000×g. The supernatant was carefully removed and passed through a 0.8 μm cell culture filter (Nalgene, Product number: 126-0020).

Equilibration of the Column

The Äkta Prime FPLC system was used in a cold room facility (6° C.). The tubing system was connected with the buffer flasks and hybridoma supernatant. The tubings were extensively rinsed with the respective buffers (50 ml minimum, at a flow rate of 50 ml/min) using the automatic washing protocols of the Äkta Prime FPLC system. The tubings were connected with the T-Gel-column, while avoiding air bubbles to get into the column. The T-gel was washed with binding buffer (minimum 50 ml) at a flow rate of 1 ml/min. The absorbance was recorded at 280 nm and the conductivity during the washing step. The column was ready to use when the absorbance reached a minimum plateau for more than 10 min and the conductivity was at approx. 140 mSi/cm.

Application of the Sample

It was changed from binding buffer to hybridoma supernatant with the buffer valve at the Äkta Prime FPLC system. The sample was applied to the column at a flow rate of 0.5 ml/min, and the flow through collected. The absorbance raised to approx. 0.2 to 0.6, indicating the absorbance of non bound proteins. In contrast, the conductivity should not change during sample application. The supernatant passed the column over night. Then it was changed from hybridoma supernatant to binding buffer with the buffer valve at the Äkta Prime FPLC system. The column was washed with binding buffer (minimum 50 ml) at a flow rate of 0.5 ml/min. The column was washed when the absorbance reached a minimum plateau for more than 10 min and the conductivity was at approx. 140 mSi/cm.

Elution of the Bound Immunoglobulins

It was changed from binding buffer to elution buffer with the buffer valve at the Äkta Prime FPLC system. The autosampler was started and fractions of 4 ml collected. The bound proteins were eluted with a flow rate of 0.5 ml/min. The absorbance and the conductivity was recorded, the latter falling to approx. 12 mSi/cm. Concomitantly the absorbance gave a peak, indicating the passing of eluted immunoglobulins. It was washed with elution buffer until the absorbance reached a minimum for more than 10 min.

Storage of the T-Gel Column

It was changed from elution buffer to storage buffer with the buffer valve at the Äkta Prime FPLC system. The column was washed with minimum 50 ml at a flow rate of 2 ml/min. The column was disconnected, sealed and stored in the cold room facility.

Every fraction of the eluted proteins was tested for the presence of immunoglobulins with an immunoglobulin-specific ELISA. Immunoglobulin-containing fractions were pooled and concentrated/dialyzed against PBS by centriprep YM-30 centrifugation/filtration units (amicon, Product number: 4306) at 1000×g, 4° C. Concentration of protein was determined by conventional Bradford assay.

Specificity of the purified cmHsp70.1 or cmHsp70.2 antibodies was assessed by:

A) FACS analysis using Hsp70 membrane-positive (Colo+, CX+) or -negative (Colo−/CX−) cells.
B) Western blotting using 10 µg of whole cell lysate (K562) separated by 10% SDS-PAGE
C) Blocking of NK-mediated killing of Hsp70 membrane-positive tumor target cells (Colo+, CX+); and/or
D) Immunohistochemistry with Hsp70 membrane-positive tumor cells; see also example 3.

For further details of one or more of the respective steps of the purification method of the present invention see, e.g., Belew et al., J. Immunol. Meth. 102 (1987), 173-182 and Nopper et al., Anal. Biochem. 180 (1989), 66-71, which refer to previous methods for the purification of monoclonal antibodies using salt-promoted adsorption and chromatography on a thiophilic adsorbent and thiophilic adsorbent for the one-step high-performance liquid chromatography, respectively.

Example 3
Characterization of Binding Properties and Biological Activity of Antibodies cm Hsp70.1 and cmHsp70.2

Antibodies cmHsp70.1 and cmHsp70.2 have been found to inhibit the cytolytic activity of cells against Hsp70 expressing tumor cells using methods described in Multhoff et al., Int. J. Cancer 61 (1995b), 272 and WO02/22656; see also FIG. 1. Due to the fact that cmHsp70.1 and cmHsp70.2 exhibit an inhibitory effect on the cytolytic activity of NK cells against Hsp70 expressing tumor cells it was of interest to map their binding epitopes. By peptide scanning (pepscan) of the C-terminal substrate binding domain within aa 384-618 the 8-mer peptide NLLGRFEL (aa 454-461) could be determined as the relevant recognition structure for the cmHsp70.1 antibody. This antibody reacts specific with Hsp70 but does not substantially cross-react with Hsc70 as determined with standard assays. The only amino acid difference of Hsp70 and Hsc70 within the 8-mer antibody binding epitope (aa 454-460) is the exchange at position 458 from arginine (R) to lysine (K). Similarly, antibody cmHsp70.2 was determined to specifically recognize a peptide consisting of the amino and sequence TKDNNLLGRFELSG.

The provision of the above described and deposited hybridomas provide a reliable source of anti-Hsp70 antibodies capable of detecting extracellular epitopes of Hsp70 on viable cells, preferably tumor cells and thereby enabling the specific detection and treatment of cells which display Hsp70 on their cell surface, in particular tumor cells and cells infected by pathogens. Thus, the present invention provides an novel class of anti-Hsp70 antibodies for use in therapy and diagnosis as well as in research in general.

The invention claimed is:

1. An isolated antibody or antigen-binding fragment thereof that binds to an extracellular localized epitope of Heat Shock Protein 70 on tumor cells, wherein said epitope comprises an amino acid sequence selected from the group consisting of NLLGRFEL (SEQ ID NO: 1) or TKDNNLLGR-FELSG (SEQ ID NO: 2) and wherein said antibody is produced by a hybridoma selected from the group consisting of the hybridomas identified by Accession Numbers DSM ACC2629 and DSM ACC2630.

2. The isolated antibody of claim 1, wherein said tumor cell is a colon tumor cell.

3. The isolated antibody or antigen-binding fragment of claim 1, which is capable of exhibiting an inhibitory effect on the cytolytic activity of NK cells against Heat Shock Protein 70 expressing tumor cells.

4. A humanized or chimeric form of the antibody of claim 1.

5. The isolated antigen-binding fragment of claim 1, which is selected from the group consisting of a single chain Fv fragment, an F(ab') fragment, an F(ab) fragment, and an F(ab')$_2$ fragment.

6. A hybridoma that produces a monoclonal antibody of claim 1.

7. The hybridoma of claim 6, selected from the group consisting of hybridoma cmHsp70.1, deposited with the DSMZ-Deutsche Sammlung von Mikroorganismen und Zelikulturen GmbH, Mascheroder Weg 1b, D-38124 Braunschweig, Germany on Nov. 14, 2003, and assigned Accession Number DSM ACC2629, and cmHsp70.2, deposited with the DSMZ-Deutsche Sammlung von Mikroorganismen und Zellkulturen GmbH on Nov. 14, 2003, and assigned Accession Number DSM ACC2630.

8. A bi- or multifunctional molecule that comprises the binding domain of an antibody of claim 1, an immunoglobulin chain thereof or a binding fragment thereof which binds an epitope of Heat Shock Protein 70, wherein said epitope comprises an amino acid sequence selected from the group consisting of NLLGRFEL (SEQ ID NO: 1) or TKDNNLLGR-FELSG (SEQ ID NO: 2), and at least one further functional domain.

9. The bi- or multifunctional molecule of claim 8, which is bispecific molecule.

10. The bispecific molecule of claim 9, which is a bispecific antibody.

11. The bi- or multifunctional molecule of claim 8, wherein said further functional domain is a cytotoxic agent or a label.

* * * * *

SEQUENCE LISTING

```
<160> NUMBER OF SEQ ID NOS: 2

<210> SEQ ID NO 1
<211> LENGTH: 8
<212> TYPE: PRT
<213> ORGANISM: Homo sapiens
<220> FEATURE:
<221> NAME/KEY: PEPTIDE
<222> LOCATION: (1)..(8)
<223> OTHER INFORMATION: Epitope of monoclonal antibody cmHsp70.1

<400> SEQUENCE: 1

Asn Leu Leu Gly Arg Phe Glu Leu
1               5

<210> SEQ ID NO 2
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: Epitope of monoclonal antibody cmHsp70.2

<400> SEQUENCE: 2

Thr Lys Asp Asn Asn Leu Leu Gly Arg Phe Glu Leu Ser Gly
1               5                   10
```